US009044403B2

(12) United States Patent
Shultz

(10) Patent No.: US 9,044,403 B2
(45) Date of Patent: Jun. 2, 2015

(54) SPORICIDAL HAND SANITIZING LOTION

(75) Inventor: Jennifer Shultz, Big Lake, MN (US)

(73) Assignee: Medivators Inc., Minneapolis, NM (US)

( * ) Notice: Subject to any disclaimer, the term of this patent is extended or adjusted under 35 U.S.C. 154(b) by 517 days.

(21) Appl. No.: 12/639,487

(22) Filed: Dec. 16, 2009

(65) Prior Publication Data

US 2010/0159028 A1    Jun. 24, 2010

Related U.S. Application Data

(60) Provisional application No. 61/138,826, filed on Dec. 18, 2008.

(51) Int. Cl.
| | |
|---|---|
| *A61K 8/22* | (2006.01) |
| *A01N 37/16* | (2006.01) |
| *A61K 8/34* | (2006.01) |
| *A61K 8/36* | (2006.01) |
| *A61K 8/92* | (2006.01) |
| *A61Q 17/00* | (2006.01) |

(52) U.S. Cl.
CPC . *A61K 8/22* (2013.01); *A01N 37/16* (2013.01); *A61K 8/345* (2013.01); *A61K 8/361* (2013.01); *A61K 8/922* (2013.01); *A61K 8/927* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 3,954,974 A | 5/1976 | Herzog et al. | |
| 4,297,298 A | 10/1981 | Crommelynck et al. | |
| 4,743,447 A | 5/1988 | Le Rouzic et al. | |
| 6,162,394 A | 12/2000 | Nicolle et al. | |
| 6,258,370 B1 | 7/2001 | Behrends et al. | |
| 6,277,414 B1 | 8/2001 | Elhaik et al. | |
| 6,284,719 B1 | 9/2001 | Simms | |
| 2003/0183540 A1* | 10/2003 | Onishi | 206/205 |
| 2005/0159324 A1 | 7/2005 | Man et al. | |
| 2005/0192197 A1 | 9/2005 | Man et al. | |
| 2006/0160712 A1 | 7/2006 | Hei et al. | |
| 2006/0177518 A1 | 8/2006 | Stevenson et al. | |
| 2006/0204467 A1* | 9/2006 | Littau et al. | 424/70.13 |
| 2006/0235080 A1 | 10/2006 | Weissbach et al. | |
| 2007/0010420 A1 | 1/2007 | Lange et al. | |
| 2007/0249712 A1 | 10/2007 | Dee et al. | |
| 2009/0074881 A1* | 3/2009 | Kielbania, Jr. | 424/616 |
| 2009/0191248 A1* | 7/2009 | Hoffman et al. | 424/402 |
| 2009/0232860 A1* | 9/2009 | Larson et al. | 424/405 |
| 2010/0003341 A1 | 1/2010 | Besendorfer | |
| 2010/0021558 A1 | 1/2010 | Dada et al. | |

FOREIGN PATENT DOCUMENTS

| | | | |
|---|---|---|---|
| EP | 1 025 759 | | 8/2000 |
| GB | 1424598 | | 2/1976 |
| GB | 1424598 A | * | 12/1976 |
| JP | 2007523892 A | | 8/2007 |
| JP | 2008531583 A | | 8/2008 |
| WO | WO0182694 A1 | | 11/2001 |
| WO | WO2005067741 A1 | | 7/2005 |
| WO | WO2006076334 A1 | | 7/2006 |
| WO | WO2006093792 A1 | | 9/2006 |
| WO | 20070014575 | | 2/2007 |

OTHER PUBLICATIONS

International Search Report and Written Opinion issued in PCT/US2009/068240, mailed Apr. 27, 2011, 15 pages.
Besse, Dr. med., "Kurzgefasster Erfahrungsbericht über die Anwendung von Wofasteril als Desinfektionsmittel und Antiseptikum am Bezirkskrankenhaus Schwerin", Kesla Hygiene AG, Feb. 5, 1985, http://www.kesla.de/cgi-bin/vm/vio.matrix?kd=a56c307a4501e86&el=697037755&typ=print, 1 page (translation attached).
Baldry, M. G., "The Bactericidal, Fungicidal and Sporicidal Properties of Hydrogen Peroxide and Peracetic Acid", Journal of Applied Bacteriology, Blackwell Publishing Ltd., Oxford, GB, vol. 54, No. 3, Jun. 1, 1983, pp. 417-423.
Baumgartner, H.J. et al., "Decomposition of concentrated Hydrogen peroxide on Silver I. Low Temperature Reaction and Kinetics", Journal of Catalysis, 2, 1963, pp. 405-414.
Maggs, F.T. et al., "Some Aspects of the Catalytic decomposition of Concentrated Hydrogen peroxide by Silver: Part 1—The Solubility and Rate of Solution of Silver", Transactions of the Faraday Society, 1958, vol. 54, pp. 1861-1870.
Swern, Daniel, "Organic Peroxy Acids-Preparation, Properties and Structure", book entitled Organic Peroxides, vol. 1, Chapter VI, Wiley-Interscience, 1970, pp. 336-337.
Yuan, Z. et al., "Kinetics of Peracetic Acid Decomposition Part I: Spontaneous Decomposition and Typical Pulp Bleaching Conditions", The Canadian Journal of Chemical Engineering, vol. 75, Feb. 1997, pp. 37-41.

* cited by examiner

*Primary Examiner* — Carlos Azpuru
*Assistant Examiner* — Casey Hagopian
(74) *Attorney, Agent, or Firm* — Faegre Baker Daniels LLP

(57) ABSTRACT

A stable, sporicidal hand sanitizer formulation is described. The formulation is a lotion including peracetic acid and one or more short chain alcohols. The lotion demonstrates an extended presence of active PAA and is capable of achieving a total kill of a bacteria in less than about 10 minutes contact time and more particularly, in about 2 minutes contact time.

25 Claims, No Drawings

SPORICIDAL HAND SANITIZING LOTION

CROSS-REFERENCE TO RELATED APPLICATION

This application claims the benefit under 35 U.S.C §119 of U.S. Provisional Application No. 61/138,826, filed on Dec. 18, 2008, entitled "SPORICIDAL HAND SANITIZER," which is herein incorporated by reference in its entirety.

TECHNICAL FIELD

The present invention relates to hand sanitizers. More particularly, the present invention relates to a stable, hand sanitizer emulsion containing a peroxy carboxylic acid having long term stability.

BACKGROUND

Currently, there are a variety of hand sanitizers available on the market. Hand sanitizers can be used in place of handwashing when hand washing is impossible or inconvenient. The currently marketed products come in one of four types: an alcohol gel which may contain some form of moisturizing agent, a lotion or gel containing chlorhexidine, a lotion or gel containing a quaternary ammonium compound, or a lotion or gel containing an antibacterial agent such as Triclosan. One drawback of the currently marketed hand sanitizers has been the limited range of efficacy against a variety of harmful microbial agents.

Spore forming bacteria, including *Clostridium difficile*, have introduced some serious challenges into the healthcare setting. These organisms can form spore coats allowing them to survive treatments with typical hand disinfection materials, such as alcohol gels, chlorhexidine gluconate scrubs, quaternary ammonium scrubs and lotions, as well as triclosan lotions and gels. Following this survival they multiply in abundance with a lack of competition. Traditional handwashing may remove a small percentage of contamination from health-care workers' (HCWs) hands, however there are numerous studies indicating that adherence to hand hygiene guidelines with traditional soap and water technique is inconsistent. HCWs have serious time pressures and require a portable and convenient means of sanitization. Development of a formula combining a sporicidal agent with cosmetic ingredients to create a sporicidal hand treatment that will be effective against vegetative and spore-forming organisms, while being non-irritating to the skin is an important development for the healthcare community.

SUMMARY

According to some embodiments, the present invention is a sporicidal hand sanitizing composition including a stable emulsion containing hydrogen peroxide, acetic acid, a barrier component, and less than about 1 wt. % fragrance capable of achieving a total kill of a spore forming bacteria in less than 10 minutes contact time. The composition is effective against *Bacillus subtilis* and *Clostridium difficile*. Additionally, the composition is effective against a non-spore forming bacteria such as *Staphyloccoccus aureus*. In some embodiments, the composition is stable or storable for at least twelve months without significant degradation of the primary active ingredients.

According to some embodiments, the present invention is a sporicidal hand sanitizing composition comprising a stable emulsion including hydrogen peroxide, acetic acid, and one or more short chain alcohols. In one embodiment, the alcohol is ethanol. The composition is able to achieve a total kill of a bacteria in about 2 minutes contact time. In one embodiment the stable emulsion is a lotion.

When formulated as a lotion, the sporicidal hand sanitizing composition demonstrates an extended presence of the peracetic acid (PAA) that is formed when hydrogen peroxide reacts with the acetic acid with significant amounts of active PAA being recovered over an extended period of time. For example, the PAA continues to be present in amounts sufficient to kill bacteria over an extended period of time, providing an extended release, long lasting effect. The presence of an alcohol in the lotion may increase the bactericidal activity of the lotion and, in larger amounts, may decrease the amount of time in which a total log kill (maximum kill) of a bacteria is achieved.

While multiple embodiments are disclosed, still other embodiments of the present invention will become apparent to those skilled in the art from the following detailed description, which shows and describes illustrative embodiments of the invention.

DETAILED DESCRIPTION

Peracetic acid, also referred to herein as PAA, is an ideal antimicrobial agent due to its high oxidizing potential. It is broadly effective against microorganisms and is not deactivated by catalase and peroxidase, the enzymes which break down hydrogen peroxide. It can be used over a wide temperature range (0-40° C.), wide pH range (3.0-7.5), in clean-in-place (CIP) processes, in hard water conditions, and is not affected by protein residues.

Peracetic acid (PAA) kills microorganisms by oxidation and subsequent disruption of their cell membrane, via the hydroxyl radical (OH). As diffusion is slower than the half-life of the radical, it will react with any oxidizable compound in its vicinity. It can damage virtually all types of macromolecules associated with a microorganism including: carbohydrates, nucleic acids mutations, lipids, and amino acids. This ultimately leads to cell lysis and true microbial death.

Finding the ideal balance of moisturizing, anti-irritant compounds that form stable emulsions, produce pleasing characteristics of feel and texture, while maintaining an effective concentration of peracetic acid to effect sporicidal action poses a challenge to formulators. Many common lotion ingredients can lead to the degradation of peracetic acid, causing the disinfectant to lose efficacy with lowering concentration. Additionally, many common lotion ingredients will not form stable emulsions in acidic, oxidizing environments such as that created by an equilibrium of acetic acid, peracetic acid, and hydrogen peroxide. Masking the strong, characteristic compound with a pleasing fragrance is also a challenge.

According to various embodiments, the present invention is a stable composition containing peracetic acid (PAA) having long term stability of the active components. The composition can be provided in the form of a gel, soap (liquid or solid), lotion, cream, ointment or other hand treatment. In other embodiments the composition can be provided as a liquid surface cleanser. The composition can contain additional additives including, but not limited to, the following: skin conditioning agents, surfactants, stabilizing agents, and combinations thereof. Additionally, the composition can contain one or more fragrances to mask or eliminate the odor from the peracetic acid. In one embodiment, the composition is provided in the form of a gel. In another embodiment, the composition is provided in the form of a lotion.

In some embodiments, the composition includes one or more carboxylic acids and one or more peroxides. The carboxylic acid included in the composition reacts with the peroxide to produce peroxycarboxylic acid. The carboxylic acid can be any carboxylic acid of sufficient solubility. Exemplary carboxylic acids include low molecular weight aliphatic carboxylic acids containing up to 6 carbon atoms in which the alkyl part of the chain can be optionally substituted. Additional exemplary carboxylic acids, include, but are not limited to, the following: acetic acid, propionic acid, formic acid, butyric acid, succinic acid, disuccinic acid, adipic acid, diadipic acid, glutaric acid, tartaric acid, citric acid, heptanoic acid, octanoic acid, nonanoic acid, decanoic acid, salilcylic acid, malic acid, lactic acid and mandelic acid. In some embodiments, the alkyl part of the chain may be optionally substituted with one or more substituents selected from halo-, nitro-, amido-, hydroxy-, carboxy-, sulpho- or phosphono-groups. Exemplary carboxylic acids in which the alkyl group is substituted include chloroacetic acid, dichloroacetic acid, trichloroacetic acid, and trifluoroacetic acid. In one embodiment, the carboxylic acid is acetic acid.

As stated above, the peroxide included in the composition reacts with the carboxylic acid to produce the peracetic acid. Exemplary peroxides include organic peroxides including benzoyl peroxide and alkyl benzoyl peroxides. In one embodiment, the peroxide is hydrogen peroxide.

In some embodiments, the composition includes one or more skin conditioning agents. Skin conditioning agents include, for example, moisturizers and barriers. Moisturizers or humectants are additives that attract moisture to the outer layers of skin to keep it moist and supple. Barriers prevent moisture already present in the skin from being lost. Exemplary skin conditioning agents include, but are not limited to, the following: glycerol, propylene glycol, sorbitol, aloe vera, lanolin or lanolin-derivatives, petrolatum, sqaulene, cetostearyl alcohol, beeswax, tricaprylin, glyceryl cocoate, isopropyl myristate, isopropyl palmitate, cetyl alcohol, stearyl alcohol, mineral oil, shea butter, safflower oil, and other moisturizers and barriers known to those of skill in the art. Other skin conditioning agents such as vitamins, anti-oxidants and other skin health compounds can also be included in the composition. Additionally, skin treatment and or anti-irritant compounds, including allantoin, trioctanoin, niacinamide, methyl sulphone, and lactose can also be included in the formulations.

In some embodiments, the composition can include one or more surfactants. The surfactant can be a non-ionic surfactant, an anionic surfactant, or a cationic surfactant. In some embodiments, a combination of surfactants may be used. In one embodiment, the surfactant is a non-ionic surfactant. In one embodiment, the surfactant is an anionic surfactant. Exemplary surfactants include, but are not limited to, the following: nonylphenol ethoxylates, alcohol ethoxylates, alcohol alkylates, sorbitan ester ethoxylates, ethoxylated alkyl-polyglucosides, alkyl ether carboxylates, fatty alcohols, ceteth-20, Octyldodeceth-20, Oleth-35, Glycereth-18, Polysorbate 20, PEG-200 Castor Oil, PEG-80 glyceral cocoate (Hetoxide GC-80), sodium lauryl sulfate, ammonium lauryl sulfate, and ethylene oxide-propylene oxide copolymers. Other surfactants known to those of skill in the art may also be used. In one embodiment, the surfactant is a non-ionic surfactant. Oleth-25, Glycereth-18 and Polysorbate-20 are exemplary non-ionic surfactants suitable for use in the various embodiments of the present invention.

In some embodiments, the composition can include one or more thickening agents. Exemplary thickening agents include, but are not limited to, the following: polyvinylpyrrolidone, xanthan gum, guar gum, clay, sodium alginate, methylcellulose, hydroxypropylcellulose, hydroxypropylmethylcellulose, carboxymethylcellulose, anionic carboxyvinyl polymers, hydroxymethylcellulose, and Carbomer 940 or 980. Other thickening agents known to those of skill in the art may also be used. In some instances emulsifying waxes may be used to thicken the composition without the need for additional thickening agents.

In some embodiments, one or more fragrances can be used to mask the odor of the PAA in the composition. The selected fragrances should be compatible with PAA. Exemplary fragrances suitable for use with PAA include, but are not limited to, the following: cuminaldehyde, cinnamic aldehyde, thymol, cineole, and piperonal. Several fragrances available from Wellington Fragrance of Livonia, Mich. have also been found to be suitable for use with PAA. These Wellington fragrances include: Rain Forest, Blackberry Sage Tea, Chai Tea, Dewberry, Dogwood, Plumeria, Tranquility, Cucumber Melon, Blackberry, Merlot, Neroli-Cedar, Sage & Chamomile, and Fresh Cotton. Any fragrance suitable for use with PAA can be included in the composition.

The various hand sanitizing compositions described above according to the various embodiments can include any number of additional components typically found in cosmetic formulations including solubilizers, emulsifyers, emollients and other components known to those of skill in the art. Additionally, it is generally recognized that some ingredients may serve a dual function, for example, some components may serve as both a surfactant and/or an emulsifier. In some instances, some components may serve as an emulsifier, a surfactant and/or a solubilizer. PEG-80 glyceral cocoate (Hetoxide GC-80) is an example of one such component that is capable of serving as an emulsifier, surfactant and/or solubilizer.

In one embodiment, the hand sanitizing composition is formulated as a lotion. When the hand sanitizing composition is formulated as a lotion, the active PAA continues to be present in an amount effective against bacterial agents over an extended period of time after application to a surface such as, for example, a skin model. Overall, the percentage of active PAA recovered over a time period ranging from about 2 minutes to about 20 minutes ranges from about 50% to about 70%. In one embodiment, the percentage of active PAA recovered after a total contact time of about 2 minutes is greater than or equal to about 70%. In another embodiment, the percentage of active PAA recovered after a contact time of about 5 minutes is greater than or equal to 60%. In still another embodiment, the percentage of active PAA recovered after a contact time of about 10 minutes is greater than or equal to about 55%. In still yet another embodiment, the percentage of active PAA recovered after 20 minutes time is greater than or equal to about 50%.

In some embodiments, the hand sanitizing composition can include one or more short chain alcohols. In one embodiment, the composition includes at least one linear or branched chain alcohol having one to six carbons. In another embodiment, the composition includes a short chain alcohol having one to three carbons. In still another embodiment, the composition includes ethanol. In yet other embodiments, the composition can include longer chain alcohols having between six and eighteen carbons. The long chain alcohols can be linear or branched.

In one embodiment, the amount of alcohol included in the composition can range from about 10 wt. % to 60 wt. % of the total weight of the composition. In another embodiment the amount of alcohol included in the composition can range from about 30 wt. % to about 60 wt. % of the total weight of the composition. In yet another embodiment, the amount of alcohol in the composition ranges from about 30 wt. % to about 40 wt. %. In still another embodiment the amount of alcohol in the composition is about 31 wt. %. In still yet another embodiment, the amount of alcohol included in the composition ranges from about 10 wt. % to about 30 wt. %.

The presence of an alcohol such as, for example, ethanol in the composition has been demonstrated to increase the bactericidal activity level of the PAA in the composition. For example, in one embodiment, a hand sanitizing composition including an alcohol such as described above according to the various embodiments, achieves a total log reduction of a bacteria in about 10 minutes or less. In another embodiment, a hand sanitizing composition including an alcohol such as described above, is capable of achieving a total log reduction of a bacteria in about 5 minutes or less contact time. In yet another embodiment, a hand sanitizing composition including an alcohol such as described above, is capable of achieving a total log reduction of a bacteria in about 2 minutes contact time.

Examples

Exemplary stable, hand sanitizing emulsions including PAA were prepared. Their formulations are provided below in Tables 1-6. All percentages are expressed as weight percents (wt/wt %).

TABLE 1

Sample 1

| Ingredient | Amount |
| --- | --- |
| Hetoxide GC-80 | 2% |
| Beeswax | 2% |
| Glycerol | 3% |
| Cetostearyl alcohol | 2% |
| Solubilizer PF | 1% |
| Hydrogen Peroxide | 4% |
| Acetic acid | 2% |
| D I water | 84% |

TABLE 2

Sample 2

| Ingredient | Amount |
| --- | --- |
| Hetoxide GC-80 | 3.00% |
| Safflower oil | 1.00% |
| Cetostearyl alcohol | 3.00% |
| Shea butter | 3.00% |
| Hydrogen Peroxide | 4.00% |
| Acetic acid | 2.00% |
| Cineole | 0.02% |
| Xanthan gum | 0.25% |
| D I water | 83.73% |

TABLE 3

Sample 3

| Ingredient | Amount |
| --- | --- |
| Propylene glycol | 10.00% |
| Glycerol | 0.50% |
| Solubilizer PF | 2.00% |
| Beeswax | 1.50% |
| Cetostearyl alcohol | 1.50% |

TABLE 3-continued

Sample 3

| Ingredient | Amount |
| --- | --- |
| Isopropyl myristate | 2.00% |
| Dimethylpolysiloxane | 1.50% |
| Lactose | 1.50% |
| "Rain Forest" fragrance | 0.11% |
| Hydrogen peroxide | 4.00% |
| Acetic acid | 2.00% |
| Deionized water | 73.39% |

TABLE 4

Sample 4

| Ingredient | Amount |
| --- | --- |
| Propylene glycol | 11.00% |
| Glycerol | 0.50% |
| Solubilizer PF | 2.00% |
| Beeswax | 1.75% |
| Cetostearyl alcohol | 1.75% |
| Isopropyl myristate | 2.00% |
| Dimethylpolysiloxane | 1.00% |
| Lactose | 1.50% |
| "Rain Forest" fragrance | 0.06% |
| Hydrogen peroxide | 4.00% |
| Acetic acid | 2.00% |
| Deionized water | 72.44% |

TABLE 5

Sample 5

| Ingredient | Amount |
| --- | --- |
| Solubilizer PF | 2.00% |
| Hest G-18-O | 2.00% |
| Hetoxol OA-35 | 1.00% |
| Beeswax | 2.00% |
| Cetostearyl alcohol | 2.00% |
| Isopropyl myristate | 1.00% |
| "Sage and Chamomile" fragrance | 0.11% |
| Hydrogen peroxide | 4.00% |
| Acetic acid | 2.00% |
| Deionized water | 83.89% |

TABLE 6

Sample 6

| Ingredient | Amount |
| --- | --- |
| Solubilizer PF | 2.00% |
| Hest G-18-O | 2.00% |
| Hetoxol OA-35 | 1.00% |
| Beeswax | 2.00% |
| Cetostearyl alcohol | 2.00% |
| Isopropyl myristate | 1.00% |
| "Sage and Chamomile" fragrance | 0.20% |
| Hydrogen peroxide | 4.00% |
| Acetic acid | 2.00% |
| Deionized water | 83.80% |

Stability

The Sample 6 presented in Table 6 was prepared by first mixing together the Solubilizer PF, Hest G-18-O, isopropyl myristate, Hetoxol OA-35, beeswax, and cetostearyl alcohol until all solids are completely melted and the mixture is homogenous in appearance. A separate mixture hydrogen peroxide, glacial acetic acid, deionized water, and fragrance was prepared and slowly added to the first mixture while stirring to form the stable emulsion. A similar process was used to prepare the other samples.

Each of the formulations described above in Tables 1-6 formed stable emulsions that did not form separate phases. In some embodiments, the formulations were observed to be stable for a period of up to about twelve months. In other embodiments, the formulations demonstrated stability over a time period of greater than twelve months. In still other embodiments, the formulations demonstrated stability over a time period ranging from about 12 months to about 25 months. Each of the formulations continues to be evaluated for stability.

Additionally, Samples 1, 2, 4 and 5 were evaluated for the amount of peracetic acid (PAA) present in the formulation at specific time intervals. The amount (ppm) of PAA in each of the formulations at the different time intervals was determined by titration. These results demonstrate that even after a time period of up to twenty-five months, a sufficient amount of PAA is present in each of the samples to achieve a total kill of a bacteria. PAA at or above 100 ppm is expected to be effective against most vegetative bacteria, including *Staphylococcus aureus* in less than 10 minutes of contact time. PAA at or above 500 ppm is expected to be sporicidal within 20 minutes of contact time. The results are summarized in Tables 7-9 below.

TABLE 7

| Time | Sample 1 | Sample 2 |
|---|---|---|
| 0 | 261* | — |
| 1 day | — | 812 |
| 6 months | 849 | 640 |
| 12 months | 708 | 654 |
| 25 months | 566 | 557 |

*not fully equilibrized

TABLE 8

| Time | Sample 4 |
|---|---|
| 0 | 623 |
| 1 month | 577 |
| 2 months | 637 |
| 4 months | 885 |
| 6.5 months | 663 |
| 9.5 months | 394 |
| 13 months | 328 |

TABLE 9

| Time | Form. 5 |
|---|---|
| 1 month | 629 |
| 5 months | 899 |
| 8 months | 630 |

Microbiological Testing

Formulations 4 and 5 (Tables 4 and 5) were evaluated for their efficacy against a variety of organisms through suspension time-kill assays. Formulation 4 was evaluated against *Clostridium difficile*. Formulation 5 was evaluated against *Bacillus subtilis* spores, *Staphylococcus aureus*, *Pseudomonas aeruginosa*, Methicillin Resistant *Staphylococcus aureus* (MRSA), Vancomycin Resistant *Enterococcus faecalis* (VRE) and compared to the efficacy of Purell® (a commercially available alcohol gel) and a benzalkonium chloride handwash (Walgreens® Foaming Hand Sanitizer).

Calculations

The log reduction in bacterial culture populations from the original solutions were calculated according to the mathematical expressions provided below:

$$\text{Test Data } CFU/\text{mL:: } \frac{(avg. \text{\# colonies found/plate dilution used})}{(\text{dilution factor})(\text{volume of neutralized solution})}{(\text{volume plated})}$$

Percent Reduction: $[1 - (\text{test survivors/test population control})] \times 100$ Log10 Reduction: Log10 (test population control) − Log10 (test survivors)

Results

TABLE 10

*Clostridium difficile*

| Time (min) | Log reduction Sample 4 |
|---|---|
| 3 | 2.5 |
| 5 | >4.8 |
| 10 | >4.8 |
| 15 | >4.8* |

*Total log reduction of spores with a 4.8 log challenge.

TABLE 11

*Staphylococcus aureus*

| | Log Reduction | | |
| Time (min) | Sample 5 | Alcohol gel | Benzalkonium chloride handwash |
|---|---|---|---|
| 0.5 | 5.7* | 5.7 | <3 |
| 1 | 5.7 | 5.7 | 3.3 |
| 2 | 5.7 | 5.7 | 5.7 |

*5.7 log reduction is the total log reduction for this test.

TABLE 12

*Pseudomonas aeruginosa*

| | Log Reduction | | |
| Time (min) | Sample 5 | Alcohol gel | Benzalkonium chloride handwash |
|---|---|---|---|
| 0.5 | 5.5* | 5.5 | <3 |
| 1 | 5.5 | 5.5 | 3.5 |
| 2 | 5.5 | 5.5 | 5.0 |

*5.5 log reduction is the total log reduction for this test.

TABLE 13

*Bacillus subtilis* (spore-former)

| | Log Reduction | |
| Time (min) | Sample 5 | Alcohol gel |
|---|---|---|
| 2 | 3.7 | — |
| 3 | 3.3 | — |
| 5 | 4.4 | 0 |
| 10 | 5.2* | — |

TABLE 13-continued

Bacillus subtilis (spore-former)

| | Log Reduction | |
|---|---|---|
| Time (min) | Sample 5 | Alcohol gel |
| 15 | — | 0 |
| 60 | — | 0 |

*5.2 log reduction is the total log reduction for this test.

TABLE 14

MRSA and VRE

| | Log Reduction | |
|---|---|---|
| Time (min) | MRSA Sample 5 | VRE Sample 5 |
| 0.5 | 5.6* | 5.3* |
| 1 | 5.6 | 5.3 |
| 2 | 5.6 | 5.3 |

*5.6 and 5.3 were the total log reductions, respectively, for this test.

Discussion

Both Samples 4 and 5 demonstrated clinical efficacy against bacteria. Sample 5 demonstrated 2.5 log reduction after 3 minutes contact time and a total kill of *Clostridium difficile* after 5 minutes contact time. Sample 5 demonstrated a total kill of *Staphylococcus aureus, Pseudomonas aeruginosa*, MRSA, and VRE after only 30 seconds of contact. Additionally, Formulation 5 demonstrated a 3.7 log reduction of *Bacillus subtilis* spores after 2 minutes contact time, a 4.4 log reduction after 5 minutes contact time, and total kill after 10 minutes contact time. It is expected that all other formulas demonstrating stable levels of PAA will be comparable in microbial efficacy.

Comparison Study

The efficacy of Sample 5 against *Mycobacterium terrae* was also evaluated using a suspension time-kill assay and compared to the efficacy of a sample containing 50% Sample 5 and 50% Purell®, and to a sample containing only Purell®. The amount of each active ingredient present in each of the samples is presented in Table 16 below. The efficacy results of the microbiological testing results are presented in Table 17.

TABLE 16

| | Sample Composition | Active |
|---|---|---|
| Sample 5 | Sample 5 | 700 ppm PAA |
| Sample 7 | 50% Sample 5: 50% Purell ® | 350 ppm PAA/31% ethanol |
| Sample 8 | Purell ® | 62% ethanol |

TABLE 17

| | Log Reduction | | |
|---|---|---|---|
| Time (min) | Sample 5 | Sample 7 | Sample 8 |
| 2 | 0 | 4.7 | 4.7 |
| 5 | 3.1 | 4.7 | NT |
| 10 | 4.7 | 4.7 | NT |

Discussion

Sample 5 demonstrated a 3.1 log reduction of *Mycobacterium terrae* after 5 minutes and a total kill after 10 minutes contact time. Sample 7, containing equal parts lotion and Purell®, achieved a total kill of the bacteria after 2 minutes contact time. Sample 8, containing only Purell®, also achieved a total kill of the bacteria after 2 minutes contact time. This data suggests that the presence of the alcohol in the sample increases the bactericidal efficacy of the PAA in the lotion (Sample 5), and reduces the amount of time it takes for a total kill of a bacteria to be achieved. Additionally, this data suggests that a lotion (Sample 5) containing an alcohol may be at least as effective as an alcohol gel.

Recovery of PAA

Sample 6 (Table 6) was also evaluated and compared to an aqueous PAA solution containing 4% hydrogen peroxide, 2% acetic acid and 94% deionized water for the percent recovery of PAA using VITRO-SKIN (IMS Inc. Portland, Me.). VITRO-SKIN is a testing substrate that effectively mimics the surface properties of human skin. It contains both optimized protein and lipid component and is designed to have topography, pH, critical surface tension and ionic strength similar to human skin. Each of the samples were evaluated for the percentage of PAA recovered at different contact times. Time 0 is the addition of the test sample to the VITRO-SKIN followed immediately by titration analysis. The samples were first analyzed in the absence of VITRO-SKIN and the average value computed. For each replicate with VITRO-SKIN the test substance was added to a container with VITRO-SKIN and the weight of substance was recorded. Following exposure time, water and sulfuric acid were added to the container and the material was titrated for PAA in the presence of VITRO-SKIN. The value (concentration) calculated from the weight added was divided by the average value for the solution (absent of VITRO-SKIN) for percent recovery. The percent recoveries were averaged over three replicates. The average percent recovery for each sample at the various contact times is reported in Table 18 below.

TABLE 18

Percent Recovery of PAA

| Contact Time | Aqueous Sample | Sample 6 (Lotion) |
|---|---|---|
| Time 0 | 61% | 100% |
| 1 minute | 33% | 91% |
| 2 minutes | — | 72% |
| 3 minutes | — | 68% |
| 5 minutes | — | 60% |
| 10 minutes | — | 56% |
| 20 minutes | — | 53% |

As demonstrated by the data presented in Table 18, the amount of PAA present in Sample 6 is present in greater amounts and for a longer period than in the aqueous solution. This suggests that the PAA composition, when formulated as a lotion, may have a longer lasting sporicidal and/or bactericidal effect due to its longer contact time with the pathogenic agent.

Unstable Formulations

Some initial compositions included concentrated PAA disinfectant solutions (Renalin) that were mixed with various thickeners and moisturizers. Three initial formulations, Samples 7-9 are described in Table 19 below.

TABLE 19

| Ingredient | Sample 7 | Sample 8 | Sample 9 |
|---|---|---|---|
| Renalin | 1.10% | 1% | 1.10% |
| Cetostearyl alcohol | 2.30% | 2% | 11% |
| Propylene glycol | 2.40% | 1% | 3% |

TABLE 19-continued

| Ingredient | Sample 7 | Sample 8 | Sample 9 |
| --- | --- | --- | --- |
| Glycerol | — | — | 4% |
| Aloe vera | — | 0.10% | 0.50% |
| Deionized water | 94.20% | 95.90% | 80.40% |

Samples 7-9 did not form stable emulsions. Each of the samples separated immediately.

Additional samples (Samples 10-15) containing 92% by volume of a commercial hand lotion (Target® Moisturizing Hand and Body Lotion), acetic acid, hydrogen peroxide (50% in water) and, in some examples, Renalin were prepared and evaluated for their stability. The composition of each sample is presented below in Table 20. Each of the Samples 10-15 separated within one week of their preparation. Additionally, Samples 14 and 15 demonstrates an approximately 50% degradation of PAA in three days.

TABLE 20

| Ingredient | 10 | 11 | 12 | 13 | 14 | 15 |
| --- | --- | --- | --- | --- | --- | --- |
| Commercial hand lotion | 92% | 92% | 92% | 92% | 99% | 98% |
| Acetic Acid | 2% | 2% | 2% | 2% | 0% | 0% |
| Hydrogen peroxide | 6% | 6% | 6% | 6% | 0% | 0% |
| Renalin | 0% | 0% | 0% | 0% | 1% | 2% |

Next, Sample 16 containing xanthan gum was prepared. The composition of Sample 16 is presented below in Table 21. Sample 16 did not form a smooth gel, contained lumps of gummy particles, and did not have an appealing appearance. Additionally, the development of PAA in the sample was inadequate.

TABLE 21

| Ingredient | Sample 16 |
| --- | --- |
| Hydrogen peroxide | 3% |
| Acetic acid | 2% |
| Thymol | 0.04% |
| Aloe | 0.50% |
| Xanthan gum | 0.50% |
| Deionized Water | 93.96% |

Several emulsions, Samples 17-20, were also attempted. The composition of each of the emulsion samples is presented in Table 22 below. Sample 17 separated into separate phases in less than 24 hours. Sample 19 separated shortly after its preparation. Sample 20 separated within 3 days after preparation. Sample 18 formed an emulsion that separated gradually over a period of several weeks. However, Sample 18 can form a semi-stable suspension when shaken or otherwise mixed.

TABLE 22

| Ingredient | Sample 17 | Sample 18 | Sample 19 | Sample 20 |
| --- | --- | --- | --- | --- |
| Hetoxol I-20-20 | — | 2.00% | — | — |
| Hetoxol OA-35 | — | 2.00% | — | — |
| Mineral oil | 24% | — | 2.00% | 2.00% |
| Beeswax | 5% | 2.00% | 2.00% | 2.00% |
| Glycerol | 3% | 2.00% | 2.00% | 2.00% |
| Cetostearyl Alcohol | 5% | 2.00% | — | — |
| Carbomer 940 | — | — | 0.25% | — |
| Xanthan Gum | — | — | — | 0.75% |

TABLE 22-continued

| Ingredient | Sample 17 | Sample 18 | Sample 19 | Sample 20 |
| --- | --- | --- | --- | --- |
| Hydrogen Peroxide | 3.75% | 4.00% | 4.00% | 4.00% |
| Acetic Acid | 1.50% | 2.00% | 2.00% | 2.00% |
| Deionized Water | 57.75% | 84.00% | 87.75% | 87.25% |

Additional emulsions, Samples 21 and 22, containing squalene and D-sorbitol were prepared. Samples 21 and 22 are summarized in Table 23 below. Sample 21 initially exhibited some stability. However, Sample 21 separated after about one month. Sample 22 separated within one week.

TABLE 23

| Ingredient | Sample 21 | Sample 22 |
| --- | --- | --- |
| Squalene | 1.00% | 1.00% |
| D-Sorbitol | 3.00% | 3.00% |
| Propylene glycol | 3.00% | 3.00% |
| Cetostearyl Alcohol | — | 2.00% |
| Hetoxol CS 20 | 2.00% | — |
| Allantoin | — | 1.00% |
| Trioctanoin | 1.00% | — |
| Hydrogen Peroxide | 4.00% | 4.00% |
| Acetic Acid | 2.00% | 2.00% |
| Cuminaldehyde | 0.02% | — |
| Piperonal | — | 0.01% |
| Deionized Water | 83.98% | 83.99% |

Three additional samples, Samples 23-25 containing methyl sulfone as an anti-irritant were prepared and evaluated. Samples 23-25 are summarized in Table 24 below. Additionally, Samples 23-25 appeared to be incapable of generating amounts of PAA greater than 500 ppm even after a period of a month. This suggests that some component in each of the sample formulations was inhibiting the formation of PAA or causing degradation of PAA in the sample.

TABLE 24

| Ingredient | Sample 23 | Sample 24 | Sample 25 |
| --- | --- | --- | --- |
| Propylene glycol | 5.00% | 10.00% | 10.00% |
| Glycerol | — | 1.00% | 1.00% |
| D-Sorbitol | 2.00% | — | — |
| Solubilizer PF | 2.00% | 2.00% | 2.00% |
| Hetoxide GC 80 | 2.00% | 2.00% | 2.00% |
| Beeswax | 1.00% | 1.50% | 1.50% |
| Cetostearyl alcohol | 1.00% | 1/50% | 1.50% |
| Trioctanoin | 1.00% | 0.50% | — |
| Allantoin | 0.50% | 0.50% | 0.50% |
| Isopropyl myristate | 2.00% | 2.00% | 2.00% |
| Squalene | 1.00% | — | — |
| Methyl sulfone | 1.00% | 1.00% | 1.00% |
| Cinnamic aldehyde | — | — | 0.09% |
| Cuminaldehyde | 0.02% | — | — |
| Piperonal | — | 0.06% | — |
| Phenoxyacetic acid | — | — | 0.05% |
| Hydrogen peroxide | 4.00% | 4.0% | 4.00% |
| Acetic acid | 2.00% | 2.00% | 2.00% |
| Deionized water | 75.48% | 71.94% | 72.36% |

Additional gel formulations were prepared using a gelling compound known as hetoxamate 6000 DB (Global Seven, Franklin, N.J.). None of the gels were stable as they formed layers having a floating precipitate. A suspension could be formed by shaking the solution vigorously before each sampling. However, the suspension would last only an hour or two, and eventually the layers containing a floating precipitate would form.

A number of fragrances were tested with a PAA solution to screen for chemical compatibility. Any fragrance that does not affect the long term stability of PAA can be included in the composition. Carvone, neryl acetate, cis-3-hexen-1-ol, d-limonene, citronellyl acetate, were found to degrade PAA in a relatively short amount of time (within 3-5 days) and therefore are not suitable for use in the formulations according to the various embodiments of the present invention. Additionally, "Blackberry Sage Tea" fragrance in combination with the vinegar-like order from the PAA in the sample was not appealing to volunteers who agreed to sample the sample lotion formulation.

Embodiments

Embodiment 1 is a topical lotion comprising: a stable emulsion including a carboxylic acid, peroxycarboxylic acid, a peroxide, a barrier component, and a fragrance, wherein the lotion does not separate into different phases and wherein the lotion achieves a total kill of a spore forming bacteria in less than about 10 minutes contact time.

The lotion according to embodiment 1, wherein the barrier component is one or more components selected from glycerol, propylene glycol, sorbitol, aloe vera, lanolin or lanolin-derivatives, petrolatum, cetostearyl alcohol, beeswax, tricaprylin, glyceryl cocoate, isopropyl myristate, or mineral oil.

The lotion according to embodiment 1, wherein the barrier component comprises mineral oil or beeswax.

The lotion according to embodiment 1, wherein the carboxylic acid is acetic acid.

The lotion according to embodiment 1, wherein the carboxylic acid is selected from the group consisting of acetic acid, propionic acid, formic acid, butyric acid, succinic acid, disuccinic acid, adipic acid, diadipic acid, glutaric acid, tartaric acid, citric acid, malic acid, lactic acid, heptanoic acid, octanoic acid, nonanoic acid, decanoic acid, salilcylic acid and mandelic acid, wherein an alkyl part of the chain is optionally substituted with one or more substituents selected from halo-, nitro-, amido-, hydroxy-, carboxy-, sulpho- or phosphono-groups.

The lotion according to embodiment 1, wherein the lotion comprises an amount of acetic acid in a range from about 1% to about 5% of the total weight of the lotion.

The lotion according to embodiment 1, wherein the lotion comprises an amount of acetic acid in a range from about 1 wt. % to about 3 wt. % of the total weight of the lotion.

The lotion according to embodiment 1, wherein the lotion comprises one or more peroxides selected from hydrogen peroxide, benzoyl peroxide, and alkyl benzoyl peroxide.

The lotion according to embodiment 1, wherein the peroxide is hydrogen peroxide.

The lotion according to embodiment 1, wherein the lotion comprises an amount of hydrogen peroxide in a range from about 3 wt. % to about 6 wt. % of the total weight of the lotion.

The lotion according to embodiment 1, wherein the lotion comprises an amount of hydrogen peroxide in a range from about 3.5 wt. % to about 4.5 wt. % of the total weight of the lotion.

The lotion according to embodiment 1, wherein the lotion further comprises a moisturizing component other than aloe vera.

The lotion according to embodiment 1, wherein the spore forming bacteria comprises *Clostridium difficile* or *Bacillus subtilis*.

The lotion according to embodiment 1, wherein the lotion does not separate into different phases for at least twelve months.

The lotion according to embodiment 1, wherein the lotion achieves a total kill of a non-spore forming bacteria in less than about thirty seconds.

The lotion according to embodiment 1, wherein the lotion achieves a total kill of a *Staphylococcus auerus* in less than about thirty seconds.

The lotion according to embodiment 1, wherein an amount of the fragrance in the lotion is less than about 1 wt. % of the total weight of the lotion.

The lotion according to embodiment 1, wherein the fragrance is one or more fragrances selected from cuminaldehyde, cinnamic aldehyde, cineole, piperonal or thymol.

The lotion according to embodiment 1, wherein the fragrance is one or more fragrances selected from Rain Forest, Blackberry Sage Tea, Chai Tea, Dewberry, Dogwood, Plumeria, Tranquility, Cucumber Melon, Blackberry, Merlot, Neroli Cedar, Sage and Chamomile or Fresh Cotton.

The lotion according to embodiment 1, further comprising an anionic surfactant.

The lotion according to embodiment 1, further comprising a non-ionic surfactant.

The lotion according to embodiment 1, further comprising one or more non-ionic surfactants selected from the group consisting of Oleth-35, Glycereth-18, Polysorbate-20.

The lotion according to embodiment 1, further comprising a thickening agent selected from the group consisting of polyvinylpyrrolidone, xanthan gum, guar gum, clay, methylcellulose, hydroxypropylcellulose, hydroxypropylmethylcellulose, carboxymethylcellulose, anionic carboxyvinyl polymers, hydroxymethylcellulose, and Carbomer 940 or 980.

The lotion according to embodiment 1, wherein the lotion achieves a 1-log reduction of a spore forming bacteria in about 4 minutes contact time.

The lotion according to embodiment 1, wherein the lotion achieves a 2-log reduction of a spore forming bacteria in about 6 minutes contact time.

The lotion according to embodiment 1, wherein the lotion achieves a total kill of a spore forming bacteria in about 5 minutes contact time.

The lotion according to embodiment 1, wherein the lotion achieves a total kill of a mycobacteria in less than about 10 minutes contact time.

The lotion according to embodiment 1, wherein the lotion achieves a total kill of a vegetative bacteria in less than about 30 seconds contact time.

The lotion according to embodiment 1, wherein the lotion achieves a total kill of a fungus in less than about 10 minutes contact time.

The lotion according to embodiment 1, further comprising a one or more linear or branched short chain alcohols.

The lotion according to embodiment 1, further comprising ethanol.

The lotion according to embodiment 1, wherein an amount of peroxycarboxylic acid recovered from a surface contacted with the lotion is at least 50% after 20 minutes of contact time.

The lotion according to embodiment 1, wherein an amount of peroxycarboxylic acid recovered from a surface contacted with the lotion is at greater than about 70% after 3 minutes of contact time.

Embodiment 2 is a sporicidal hand sanitizer composition comprising a stable emulsion including hydrogen peroxide, acetic acid, peracetic acid, a barrier component, and fragrance, wherein the composition achieves a total kill of a spore forming bacteria in less than 10 minutes contact time and does not separate into different phases.

The composition according to embodiment 2, wherein the composition comprises an amount of fragrance less than about 1 wt. % the total weight of the composition The composition according to embodiment 2, wherein the barrier component comprises mineral oil or beeswax.

The composition according to embodiment 2, wherein the barrier component comprises one or more components selected from glycerol, propylene glycol, sorbitol, aloe vera, lanolin or lanolin-derivatives, petrolatum, cetostearyl alcohol, beeswax, tricaprylin, glyceryl cocoate, isopropyl myristate, or mineral oil.

The composition according to embodiment 2, wherein the composition comprises an amount of hydrogen peroxide in a range from about 3 wt. % to about 6 wt. % of the total weight of the composition.

The composition according to embodiment 2, wherein the composition comprises an amount of hydrogen peroxide in a range from about 3.5 wt. % to about 4.5 wt. % of the total weight of the composition.

The composition according to embodiment 2, wherein the composition comprises an amount of acetic acid in a range from about 1 wt. % to about 5 wt. % of the total weight of the composition.

The composition according to embodiment 2, wherein the composition comprises an amount of acetic acid in a range from about 1 wt. % to about 3 wt. % of the total weight of the composition.

The composition according to embodiment 2, wherein the composition further comprises a moisturizing component other than aloe vera.

The composition according to embodiment 2, wherein the spore forming bacteria comprises *Clostridium difficile* or *Bacillus subtilis*.

The composition according to embodiment 2, wherein the composition has a stability of at least twelve months.

The composition according to embodiment 2, wherein the composition achieves a total kill of a non-spore forming bacteria in less than about thirty seconds.

The composition according to embodiment 2, wherein the composition achieves a total kill of *Staphylococcus aureus*.

The composition according to embodiment 2, further comprising a surfactant.

The composition according to embodiment 2, further comprising a thickening agent.

The composition according to embodiment 2, wherein the composition achieves a 1-log reduction of a spore forming bacteria in about 4 minutes contact time.

The composition according to embodiment 2, wherein the composition achieves a 2-log reduction of a spore forming bacteria in about 6 minutes contact time.

The composition according to embodiment 2, wherein the composition achieves a total kill of a spore forming bacteria in about 5 minutes contact time.

Embodiment 3 is a sporicidal hand sanitizing composition comprising: a stable emulsion including a peroxide, a carboxylic acid, a peroxycarboxylic acid and one or more short chain alcohols having one to six carbons.

The composition according to embodiment 3, wherein the composition achieves a total kill of a bacteria in about 2 minutes contact time.

The composition according to embodiment 3, wherein the composition achieves a total kill of a bacteria in about 10 minutes or less.

The composition according to embodiment 3, wherein the composition achieves a total kill of a bacteria in about 5 minutes or less.

The anti-microbial hand sanitizing composition according to embodiment 3, wherein the composition is a lotion.

The composition according to embodiment 3, wherein the one or more short chain alcohols includes one to three carbons.

The anti-microbial hand sanitizing composition according to embodiment 3, wherein the one or more short chain alcohols comprises ethanol.

The anti-microbial hand sanitizing composition according to claim 58, further comprising about 62 wt. % ethanol.

The anti-microbial hand sanitizing composition according to claim 58, further comprising about 50 wt. % ethanol.

The anti-microbial hand sanitizing composition according to claim 58, further comprising about 31 wt. % ethanol.

The composition according to embodiment 3, wherein the composition achieves a total kill of a mycobacteria in less than about 10 minutes contact time.

The composition according to embodiment 3, wherein the composition achieves a total kill of a vegetative bacteria in less than about 30 seconds contact time.

The composition according to embodiment 3, wherein the composition achieves a total kill of a fungus in less than about 10 minutes contact time.

The composition according to embodiment 3, wherein an amount of peroxycarboxylic acid recovered from a surface contacted with the composition is at least 50% after 20 minutes of contact time.

The composition according to embodiment 3, wherein an amount of peroxycarboxylic acid recovered from a surface contacted with the composition is at greater than about 70% after 3 minutes of contact time.

The composition according to embodiment 3, wherein the composition is any one of a soap, gel, lotion, cream, ointment or liquid surface cleanser.

Embodiment 4 is a method of making a stable, sporicidal hand sanitizing composition including a peroxide, a carboxylic acid, and a barrier component, wherein the composition does not undergo a phase separation, the method comprising the steps of:
a) preparing a first mixture including the barrier component;
b) stirring the first mixture until the first mixture is homogenous in appearance;
c) preparing a second aqueous mixture comprising the peroxide, the carboxylic acid, water and fragrance; and
d) adding the second aqueous mixture to the first mixture containing the barrier component while stirring to form an emulsion.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

I claim:

1. A sporicidal hand sanitizer lotion composition in a stable emulsion form, the composition consisting of:
at least one carboxylic acid selected from the group consisting of acetic acid, propionic acid, citric acid and glutaric acid;
at least one peroxycarboxylic acid;
hydrogen peroxide;
at least one nonionic surfactant;
at least one skin conditioning agent;
at least one fragrance;
water; and
optionally one or more skin treatment compounds, antirritant compounds, anionic surfactants, cationic surfactants, thickening agents, solubilizers, emulsifiers, or emollients or a combination thereof, wherein the one or more skin treatment compounds is selected from the group consisting of allantoin, trioctanoin, niacinamide, methyl sulphone and lactose, wherein after a storage period of 12 months the composition does not separate into different phases and achieves a total kill of a spore forming bacteria in less than about 10 minutes contact time.

2. The composition according to claim 1, wherein the skin conditioning agent is one or more components selected from glycerol, propylene glycol, sorbitol, aloe vera, lanolin or lanolin-derivatives, petrolatum, cetostearyl alcohol, beeswax, tricaprylin, glyceryl cocoate, isopropyl myristate, or mineral oil.

3. The composition according to claim 1, wherein the skin conditioning agent is mineral oil or beeswax.

4. The composition according to claim 1, wherein the carboxylic acid is acetic acid.

5. The composition according to claim 1, wherein acetic acid is present in an amount from about 1% to about 5% of the total weight of the composition.

6. The composition according to claim 1, wherein hydrogen peroxide is present in an amount from about 3 wt. % to about 6 wt. % of the total weight of the composition.

7. The composition according to claim 1, wherein at least one skin conditioning agent is a moisturizing component other than aloe vera.

8. The composition according to claim 1, wherein the peroxycarboxylic acid is present in the composition in an amount effective to achieve a total kill of a spore-forming bacteria for at least twelve months.

9. The composition according to claim 1, wherein the composition achieves a total kill of a non-spore forming bacteria in less than about thirty seconds.

10. The composition according to claim 1, wherein an amount of the fragrance in the composition is less than about 1 wt. % of the total weight of the composition.

11. The composition according to claim 1, wherein the fragrance is one or more fragrances selected from cuminaldehyde, cinnamic aldehyde, cineole, piperonal or thymol.

12. The composition according to claim 1, wherein the fragrance is one or more fragrances selected from Rain Forest, Blackberry Sage Tea, Chai Tea, Dewberry, Dogwood, Plumeria, Tranquility, Cucumber Melon, Blackberry, Merlot, Neroli Cedar, Sage and Chamomile or Fresh Cotton.

13. The composition according to claim 1, wherein the nonionic surfactant is selected from the group consisting of Oleth-35, Glycereth-18, Polysorbate-20, and combinations thereof.

14. The composition according to claim 1, wherein at least one thickening agent is present.

15. The composition according to claim 1, wherein the composition achieves a 1-log reduction of a spore forming bacteria in about 4 minutes contact time.

16. The composition according to claim 1, wherein the composition achieves a 2-log reduction of a spore forming bacteria in about 6 minutes contact time.

17. The composition according to claim 1, wherein the composition achieves a total kill of a spore forming bacteria in about 5 minutes contact time.

18. The composition according to claim 1, wherein the composition achieves a total kill of a mycobacteria in less than about 10 minutes contact time.

19. The composition according to claim 1, wherein the composition achieves a total kill of a vegetative bacteria in less than about 30 seconds contact time.

20. The composition according to claim 1, wherein the composition achieves a total kill of a fungus in less than about 10 minutes contact time.

21. The composition according to claim 1, wherein an amount of peroxycarboxylic acid recovered from a surface contacted with the composition is at least 50% after 20 minutes of contact time.

22. The composition according to claim 1, wherein an amount of peroxycarboxylic acid recovered from a surface contacted with the composition is at greater than about 70% after 3 minutes of contact time.

23. A sporicidal hand sanitizer lotion composition in a stable emulsion form, the composition consisting of:
at least one carboxylic acid selected from the group consisting of acetic acid, propionic acid, citric acid and glutaric acid;
at least one peroxycarboxylic acid;
hydrogen peroxide;
at least one nonionic surfactant;
at least one skin conditioning agent;
at least one fragrance;
water; and
optionally one or more skin treatment compounds, antirritant compounds, anionic surfactants, cationic surfactants, thickening agents, solubilizers, emulsifiers, or emollients or a combination thereof, wherein the one or more skin treatment compounds is selected from the group consisting of allantoin, trioctanoin, niacinamide, methyl sulphone and lactose.

24. The composition according to claim 23, wherein acetic acid is present in an amount from about 1% to about 5% of the total weight of the composition.

25. The composition according to claim 23, wherein hydrogen peroxide is present in an amount from about 3 wt. % to about 6 wt. % of the total weight of the composition.

* * * * *